(12) United States Patent
Murray et al.

(10) Patent No.: US 11,737,968 B2
(45) Date of Patent: Aug. 29, 2023

(54) INSECT CONTROL PRODUCT FOR CATS AND DOGS

(71) Applicant: Pouch Pac Innovations, LLC, Sarasota, FL (US)

(72) Inventors: R. Charles Murray, Sarasota, FL (US); John Harlin, Sarasota, FL (US)

(73) Assignee: Pouch Pac Innovations, LLC, Sarasota, FL (US)

(*) Notice: Subject to any disclaimer, the term of this patent is extended or adjusted under 35 U.S.C. 154(b) by 0 days.

(21) Appl. No.: 17/551,721

(22) Filed: Dec. 15, 2021

(65) Prior Publication Data

US 2022/0183959 A1    Jun. 16, 2022

Related U.S. Application Data

(60) Provisional application No. 63/125,683, filed on Dec. 15, 2020.

(51) Int. Cl.
*A61K 8/92*    (2006.01)
*A61Q 17/02*    (2006.01)
*A61K 8/06*    (2006.01)

(52) U.S. Cl.
CPC ............. *A61K 8/922* (2013.01); *A61K 8/062* (2013.01); *A61Q 17/02* (2013.01)

(58) Field of Classification Search
None
See application file for complete search history.

(56) References Cited

U.S. PATENT DOCUMENTS

2017/0127675 A1* 5/2017 Brown .................. A01N 43/16
2019/0274314 A1* 9/2019 Teevan .................. A01N 65/22

* cited by examiner

*Primary Examiner* — Nannette Holloman
(74) *Attorney, Agent, or Firm* — Fishman Stewart PLLC

(57) ABSTRACT

A topical insect repellent and insecticide composition for cats and dogs that includes a lotion including active and inert ingredients. The active ingredients include cedarwood oil, rosemary oil, and thyme oil and the inert ingredients include sunflower oil, isopropyl myristate, decanoic acid, lauric acid, water, vanillin, lecithin, and triethyl citrate.

6 Claims, 7 Drawing Sheets

INSECT CONTROL PRODUCT FOR CATS AND DOGS

CROSS-REFERENCE TO RELATED APPLICATIONS

The instant application claims priority to U.S. Provisional Application Ser. No. 63/125,683 filed Dec. 15, 2020 the entire contents of which are incorporated herein by reference.

FIELD OF THE INVENTION

The instant application is directed to a formulation for a topical insect repellent for animals.

BACKGROUND OF THE INVENTION

Insect bites often cause annoying reactions in animals. Additionally, insect bites are a vector for many types of disease including: malaria, Dengue Fever, Chikungunya, West Nile and Zika viruses as well as other forms of disease.

There is a need to prevent insects from biting a host to lessen the discomfort of a bite reaction and to prevent the potential spread of a disease.

Accordingly, a natural non-toxic ingredient based topical product that prevents bites to animals and repels insects would be desirable.

SUMMARY OF THE INVENTION

In one aspect, there is disclosed a topical insect repellent composition for cats and dogs that includes a lotion including active and inert ingredients. The active ingredients include cedarwood oil, rosemary oil, and thyme oil and the inert ingredients include sunflower oil, isopropyl myristate, decanoic acid, lauric acid, water, vanillin, lecithin, and triethyl citrate.

In another aspect, there is disclosed a topical insecticide composition for cats and dogs that includes a lotion including active and inert ingredients. The active ingredients include cedarwood oil, rosemary oil, and thyme oil and the inert ingredients include sunflower oil, isopropyl myristate, decanoic acid, lauric acid, water, vanillin, lecithin, and triethyl citrate.

In a further aspect, there is disclosed a method of repelling insects on cats or dogs applying a lotion composition to a cat or dog and exposing insects to the lotion, the lotion including active and inert ingredients, wherein the active ingredients include cedarwood oil, rosemary oil, and thyme oil and the inert ingredients include sunflower oil, isopropyl myristate, decanoic acid, lauric acid, water, vanillin, lecithin, and triethyl citrate.

DETAILED DESCRIPTION OF THE PREFERRED EMBODIMENTS

Figure 1:
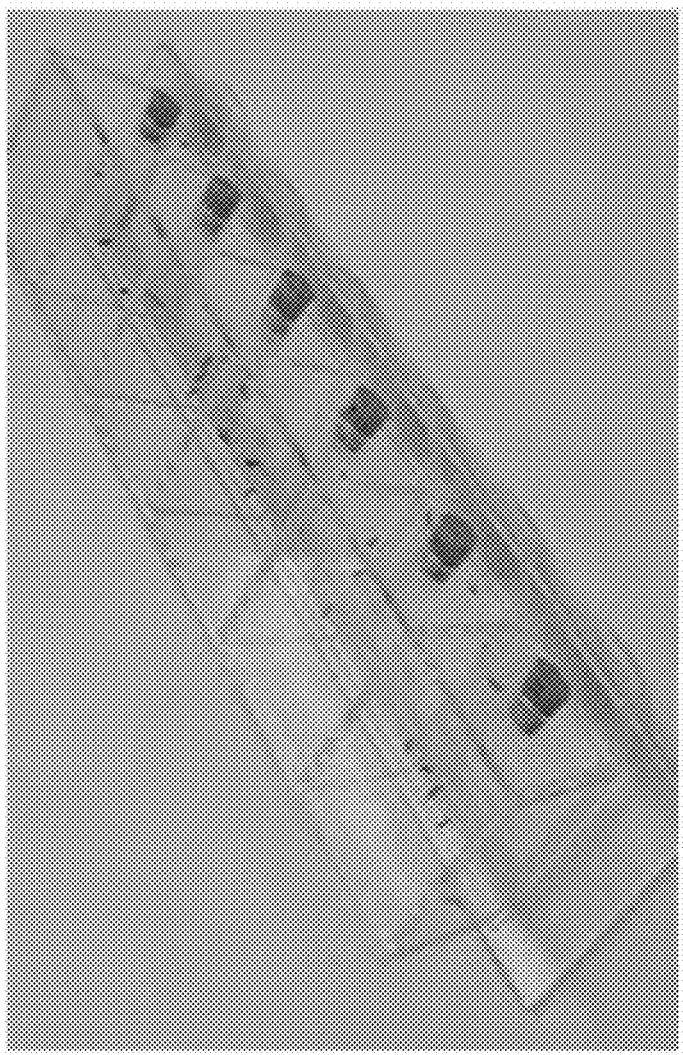
FIG. 1 is a graphical representation of an experimental apparatus used for testing.
Figure 2:
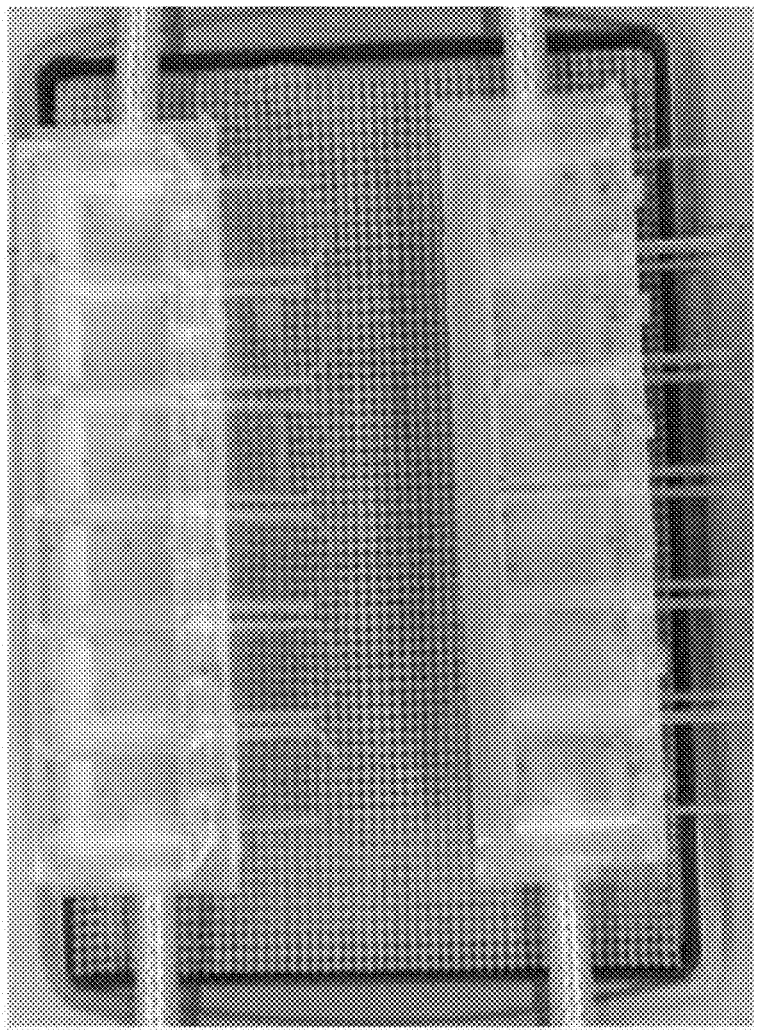
FIG. 2 is a graphical depiction of an experimental apparatus positioned over a blood source.
Figure 3:
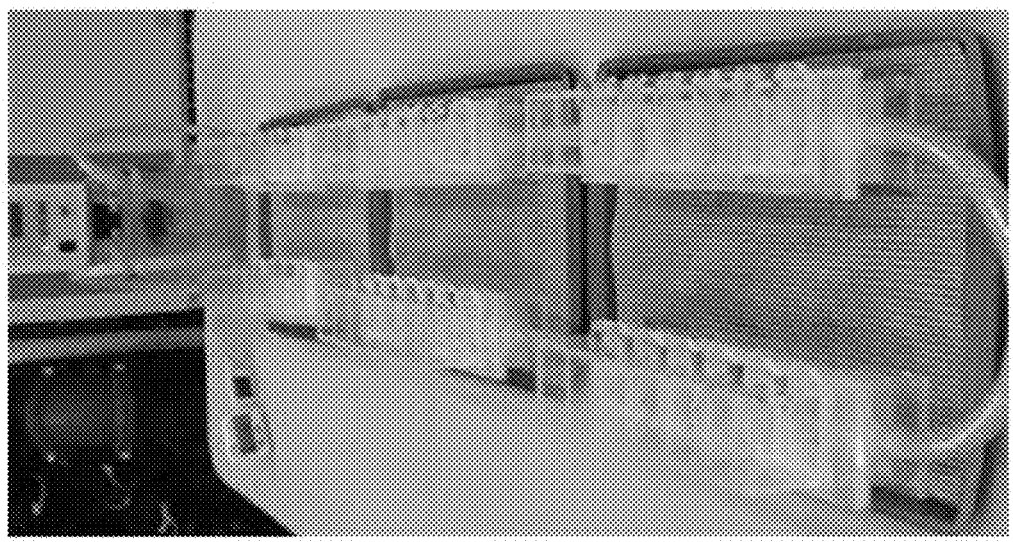
FIG. 3 is a graphical representation of an experimental apparatus including a circulating pump providing warm water to the testing apparatus.

Insect bites may transmit diseases and cause reactions to animals that are bitten. Various repellant compositions have been utilized in prior art repellant compositions. One such repellant, DEET, is often used in mosquito repellant compositions. DEET has been questioned as to its toxicity in higher amounts. There is therefore a need in the art for an improved and safe topical insect repellant composition.

Further, various animals such as cats and dogs may have different physiologies and characteristics requiring different types of repellents. It would therefore be beneficial to have a composition that repels insects for both cats and dogs.

In one aspect, there is disclosed herein a formulation that may be utilized as a topical lotion or spray to repel insects. The formulation may include organic and chemical-free compositions that will protect animals from biting and blood-seeking insects such as mosquitos, flies and other biting insects.

Example 1

| Ingredient Active | Percentage | Range |
|---|---|---|
| Cedarwood Oil | 2.5 | 1.5 to 3.5 |
| Rosemary Oil | 3 | 2 to 4 |
| thyme Oil | 2 | 1 to 3 |
| Ingredient Inert | | |
| Water | 49.5 | 40 to 60 |
| Sunflower Oil | 14 | 10 to 20 |
| Isopropyl myristate | 14 | 10 to 20 |
| Decanoic acid | 5 | 3 to 7 |
| Laurie acid | 5 | 3 to 7 |
| Vanillin | 4 | 2 to 6 |
| Triethyl Citrate | 3 | 2 to 4 |
| Lecithin | 0.5 | 0.3 to 0.7 |

The composition may include edible oil such as sunflower oil, cedarwood oil, thyme oil, rosemary oil, isopropyl myristate, decanoic acid, lauric acid, vanillin, triethyl citrate, water and lecithin.

The water may be present in an amount of from 40 to 60% by weight. The sunflower oil may be present in an amount of from 10 to 20% by weight. The cedarwood oil may be present in an amount of from 1.5 to 3.5% by weight. The thyme oil may also be present in an amount of from 1 to 3% by weight. The rosemary oil may also be present in an amount of from 2 to 4% by weight. The decanoic acid may be present in an amount of from 3 to 7% by weight. Laurie acid may be present in an amount of from 3 to 7% by weight. Isopropyl myristate may be present in an amount of from 10 to 20% by weight. Vanillin may be present in an amount of from 2 to 6% by weight. Triethyl citrate may be present in an amount of from 2 to 4% by weight. Lecithin may be present in an amount of from 0.3 to 0.7% by weight. The weight percentages are based on a total weight of the composition.

As described above, the composition may include active ingredients and inactive ingredients. The cedarwood oil, thyme oil, and rosemary oil may be classified as active ingredients wherein isopropyl myristate, decanoic acid, lauric acid, vanillin, triethyl citrate, and lecithin may be considered inert or inactive ingredients.

The composition was made according to the following procedure. The Sunflower oil was heated from room temperature to 145 to 160 degrees F. in a mixing vat under agitation. The lecithin, vanillin and three quarters of the amount of water were added to the composition when the temperature approaches 100 F. The mixture is heated and agitated until about 125 degrees F. and a shearing mechanism is activated and maintained until the mixture contains no grit. Next, decanoic acid, lauric acid, isopropyl myristate, and triethyl citrate, are added to the composition under agitation. The composition is maintained under agitation. Cedarwood oil, thyme oil and rosemary oil and the remaining one quarter of the water is then added and the composition cools to about 125-130 F. The composition is agitated and sheared for a specified time dependent upon the size of the batch.

The efficacy of the formulas provided in the examples may be attributed to various properties. In one aspect, the fatty acids and isopropyl myristate present in the composition are not volatile and provide a long lasting product when applied. Further, the acids Decanoic Acid (C10:0), Laurie Acid (C12:0) may have properties that deter or repel insects.

Testing

Figure 4:
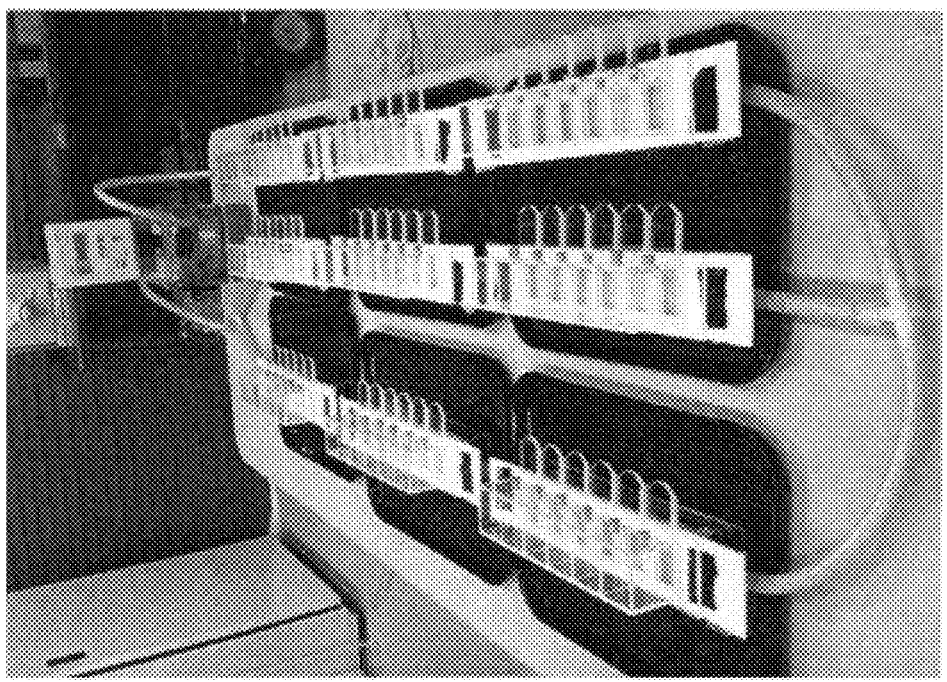
FIG. 4 is a graphical depiction of an experimental apparatus positioned over a blood source.
Figure 5:
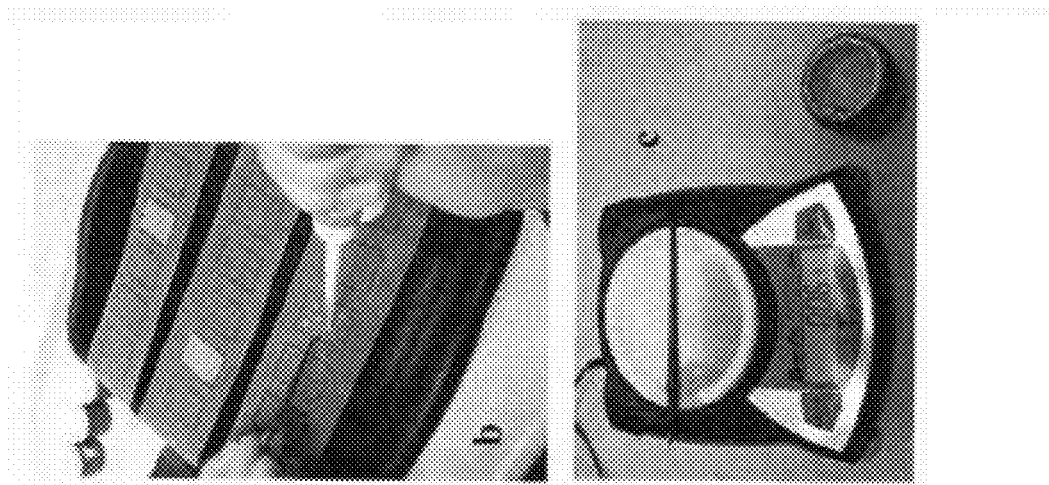
FIG. 5 is a graphical depiction of an experimental apparatus and application of repellents.
Figure 5:
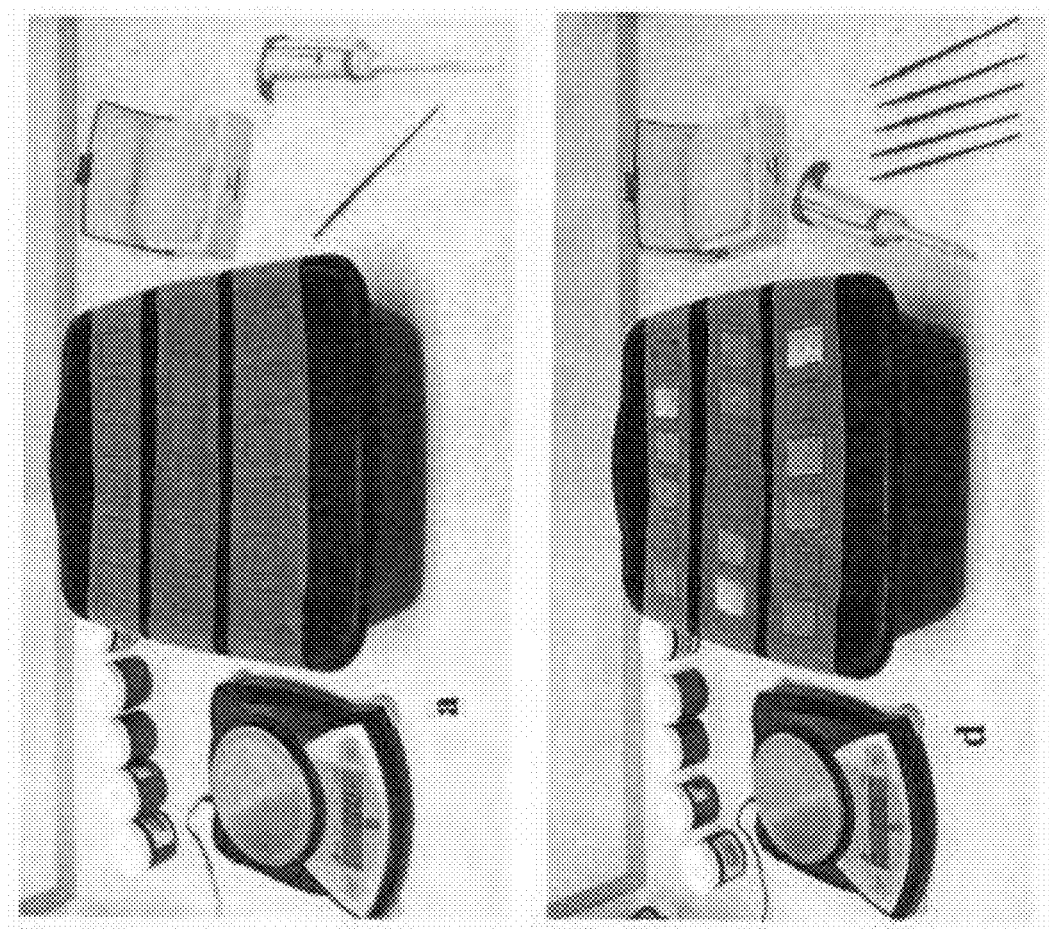
Figure 6:
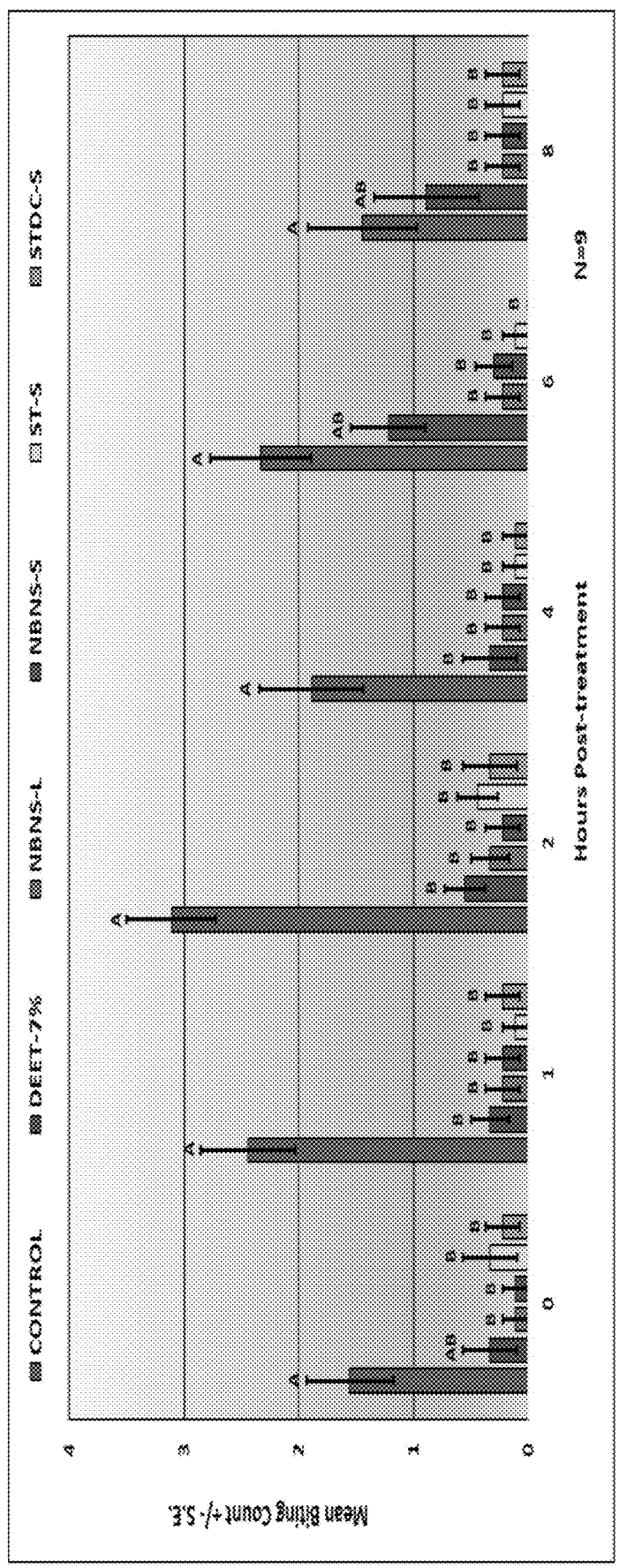
FIG. 6 is a graph of the mean bite count as a function of time for repellents.
Figure 7:
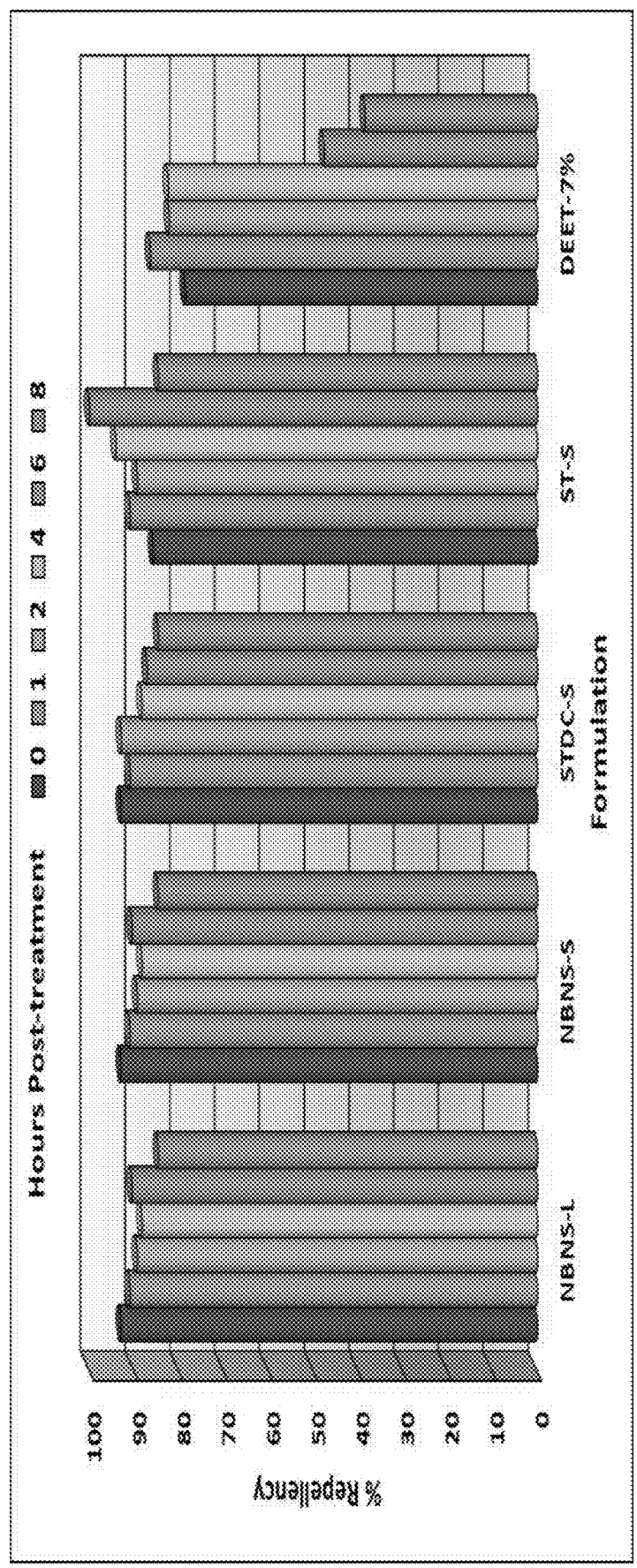
FIG. 7 is a graph of the % repellency as a function of time for repellents.

The deterrent effect of the above-described compositions (represented as STDC-S (example 1) in FIGS. 6-7) was tested in a controlled environment. In vitro laboratory tests were conducted and measured and compared to DEET and nontreated control groups for yellow fever mosquitos, *Aedes aegypti*. The repellency of the formulations were compared to a DEET standard, and a non-treated control against yellow fever mosquitoes, *Aedes aegypti*. The examples were performed in a temperature-controlled laboratory following techniques as disclosed in Klun, J. A., M. A. Kramer, A. Zhang, S. Wang, and M. Debboun. 2008. A quantitative in vitro assay for mosquito deterrent activity without human blood cells. J Am. Mosq. Contr. Assoc. 24:508-512. Bioassays were conducted in nine, six-chambered Plexiglasss K&D modules interconnected with hoses to a water bath supplied with a temperature-controlled inversion circulator as displayed in (FIG. 5). Five colony-reared female *Aedes aegypti* were aspirated into each chamber (FIG. 1). Nine replications of the following treatments were randomly assigned to the chambers: STDC-S; Positive control—7% DEET standard and Negative control—Non-treated. Repellents were applied to nine ca. 2"×2"×9" strips of organdy cloth and spread with a small paint brush over 12 cm' ink-pen-demarcated rectangles drawn on the strips with a flat plastic template. A micropipette set at 27.6 µl was used to apply liquid repellents, while creams were applied at 0.06 g (FIG. 5 a-d). Treated clothes were taped to flat plastic templates with openings aligning with lower Plexiglasss bases. The lower Plexiglasss bases contained shallow surface wells that were filled with a blood substitute (CDTA and ATP) and covered with moistened collagen membranes. The blood substitute was heated to 38° C. with water pumped through hose lines attached to the lower base and the water bath. The plastic templates were fitted between the K&D modules and lower Plexiglasss bases (FIG. 4). Mosquitoes were exposed to the treated surfaces by opening the K&D module sliding doors for 90-second biting counts at five post-treatment time intervals (0, 1, 2, 4 & 6 hrs) (FIG. 1). Fresh mosquitoes were aspirated into the chambers for each time interval. The dependent variable was biting count mean. Treatment and module means were independent variables. Biting counts as well as log and square root transformed biting counts by treatment were examined for normality with SAS PC Proc Univariate. The variance in biting count means by treatment and time intervals was statistically analyzed with SAS Proc ANOVA and statistically tested for significant differences with Tukey's Studentized Range test at $p<0.05$ and charted with 95% Confidence Intervals (C.I.). Average % repellency was calculated with the following formula and charted by treatment and time interval: (Control Avg. Biting Count−Treatment Avg. Biting Count)÷Control Avg. Biting Count×100.

Normality Tests:

Biting counts by treatment were found to follow closer to a normal distribution compared to log or square root transformed data. Consequently, all statistical analysis was conducted on non-transformed data.

Biting Count and Repellency:

There were no significant differences in average biting counts among the nine K&D modules. Biting counts in the controls were significantly greater than all formulations at 0, 1, 2, 6, and 8 hrs. post-treatment (FIG. 6). Cutters 7% DEET lost effectiveness at 6 & 8 hrs. with biting counts not differing significantly than the control. As measured by percent repellency, all formulations performed better than the Cutter Skinsations 7% DEET at all time intervals (FIG. 7). Repellency for STDC-S ranged from 86-100% from 0-6 hrs., respectively, and decreased to 85% at 8 hrs. The greatest repellency for Cutter Skinsations was 87% at 1 hr. post-treatment. Repellency was slightly lower through 4 hrs. and then dropped to 48% and 39%, respectively, at 6 and 8 hrs. post-treatment. All formulations outperformed Cutter Skinsations 7% DEET in repellency and duration.

Insect and Tick Testing

Testing was performed on the formula of example 1 for its repellency and insecticidal properties.

Various live tick species were purchased from Oklahoma State University. Five ticks of the identified species were placed in containers and then exposed to the formula of example 1. The species of tick and results are presented in Table 2 below.

TABLE 2

| Tick Species | |
|---|---|
| Dermacentor variabilis | 1 minute after spray, all animals paralyzed; 7 minutes after spray, all dead |
| Amblyomma americanum | 1 minute after spray, all animals paralyzed; 7 minutes after spray, all dead |
| Rhipicephalus sanguineus | 1 minute after spray, all animals paralyzed; 7 minutes after spray, all dead |
| Ixodes scapularis | 1 minute after spray, all animals paralyzed; 3 minutes after spray, all dead |

As can be seen from the above results, the formula of example 1 acts as an insecticide for ticks that have been sprayed with the composition of formula 1.

The formula of example 1 was applied to cats and dogs that had flea and tick infestations. After application to the animals, it was observed that fleas and ticks dropped off of the animals and were dead after 5 to 10 minutes of application. This result is consistent with the observations in Table 2.

The formula of Example 1 provides a natural repellant and insecticide composition for both cats and dogs. The formula of Example 1 is not toxic to humans and can be applied without protection to the human.

The invention claimed is:

1. A topical insect repellent composition for cats and dogs comprising:
a lotion including active and inert ingredients, wherein the active ingredients include cedarwood oil, rosemary oil, and thyme oil and the inert ingredients include sunflower oil, isopropyl myristate, decanoic acid, lauric acid, water, vanillin, lecithin, and triethyl citrate.

2. The topical mosquito repellent composition of claim 1 wherein the water is present in an amount of from 40 to 60% by weight, the sunflower oil is present in an amount of from 10 to 20% by weight, the cedarwood oil is present in an amount of from 1.5 to 3.5% by weight, the thyme oil is present in an amount of from 1 to 3% by weigh, the rosemary oil is present in an amount of from 2 to 4% by weight, the decanoic acid is present in an amount of from 3 to 7% by weight, the lauric acid is present in an amount of from 3 to 7% by weight, the isopropyl myristate is present in an amount of from 10 to 20% by weight, the vanillin is present in an amount of from 2 to 6% by weight, the triethyl citrate is present in an amount of from 2 to 4% by weight and the lecithin may be present in an amount of from 0.3 to 0.7% by weight, where the weight percentages are based on a total weight of the composition.

3. A topical insecticide composition for cats and dogs comprising:
a lotion including active and inert ingredients, wherein the active ingredients include cedarwood oil, rosemary oil, and thyme oil and the inert ingredients include sunflower oil, isopropyl myristate, decanoic acid, lauric acid, water, vanillin, lecithin, and triethyl citrate.

4. The topical insecticide composition of claim 3 wherein the water is present in an amount of from 40 to 60% by weight, the sunflower oil is present in an amount of from 10 to 20% by weight, the cedarwood oil is present in an amount of from 1.5 to 3.5% by weight, the thyme oil is present in an amount of from 1 to 3% by weigh, the rosemary oil is present in an amount of from 2 to 4% by weight, the decanoic acid is present in an amount of from 3 to 7% by weight, the lauric acid is present in an amount of from 3 to 7% by weight, the isopropyl myristate is present in an amount of from 10 to 20% by weight, the vanillin is present in an amount of from 2 to 6% by weight, the triethyl citrate is present in an amount of from 2 to 4% by weight and the lecithin may be present in an amount of from 0.3 to 0.7% by weight, where the weight percentages are based on a total weight of the composition.

5. A method of repelling insects on cats or dogs comprising:
applying a lotion composition to a cat or dog and exposing insects to the lotion, the lotion including active and inert ingredients, wherein the active ingredients include cedarwood oil, rosemary oil, and thyme oil and the inert ingredients include sunflower oil, isopropyl myristate, decanoic acid, lauric acid, water, vanillin, lecithin, and triethyl citrate.

6. The method of claim 5 wherein the water is present in an amount of from 40 to 60% by weight, the sunflower oil is present in an amount of from 10 to 20% by weight, the cedarwood oil is present in an amount of from 1.5 to 3.5% by weight, the thyme oil is present in an amount of from 1 to 3% by weigh, the rosemary oil is present in an amount of from 2 to 4% by weight, the decanoic acid is present in an amount of from 3 to 7% by weight, the lauric acid is present in an amount of from 3 to 7% by weight, the isopropyl myristate is present in an amount of from 10 to 20% by weight, the vanillin is present in an amount of from 2 to 6% by weight, the triethyl citrate is present in an amount of from 2 to 4% by weight and the lecithin may be present in an amount of from 0.3 to 0.7% by weight, where the weight percentages are based on a total weight of the composition.

\* \* \* \* \*